United States Patent [19]

Smith

[11] Patent Number: 5,420,345
[45] Date of Patent: May 30, 1995

[54] PROCESS FOR PREPARING CARBOXYLIC ACIDS

[75] Inventor: Warren J. Smith, Middlesex, United Kingdom

[73] Assignee: BP Chemicals Limited, London, England

[21] Appl. No.: 143,458

[22] Filed: Oct. 26, 1993

[30] Foreign Application Priority Data

Nov. 5, 1992 [GB] United Kingdom ............. 9223170

[51] Int. Cl.⁶ .................. C07C 1/20; C07C 51/12
[52] U.S. Cl. .................. 562/519; 562/517
[58] Field of Search .......... 562/519, 517; 502/62, 502/74, 66; 423/239, 351, 212

[56] References Cited

U.S. PATENT DOCUMENTS

| | | | |
|---|---|---|---|
| 3,855,307 | 12/1974 | Rony et al. | 260/604 |
| 4,297,328 | 10/1981 | Ritscher et al. | 423/213.2 |
| 4,444,898 | 4/1984 | Schwartz | 502/62 |
| 4,612,387 | 9/1986 | Feitler | 560/232 |
| 5,149,512 | 9/1992 | Li et al. | 423/239 |
| 5,187,133 | 2/1993 | Yoshinari et al. | 502/66 |
| 5,258,549 | 11/1993 | Pimblett | 562/519 |

FOREIGN PATENT DOCUMENTS

| | | |
|---|---|---|
| 0353722 | 2/1990 | European Pat. Off. |
| 3606169 | 2/1986 | Germany |
| 06169 | 8/1987 | Germany |
| 185453 | 3/1970 | United Kingdom |
| 1185453 | 3/1970 | United Kingdom |
| 1277242 | 6/1972 | United Kingdom |

OTHER PUBLICATIONS

Olsson, R. W. et al, Inorganic Chemistry, vol. 16, No. 3, pp. 651–654, 1977.

Bagno, Alessandro et al, J. Org. Chem, 1990, 55, 4284–4289.

The Chemistry Society of Japan, pp. 2047–2050, 1984, *Vapor Phase Carbonylation of Methanol with Solid Acid Catalysts.*

Journal of Catalysts 71, 233–243 (1981), S. Lars T. Andersson, Department of Chemical Technology, Lund Institute of Technology, Chemical Center, Lind, Sweden, *Studies by ESCA of Supported Rhodium Catalysts Related to Activity for Methanol Carbonylation,* and Michael S. Scurrell, Institute for Kemiindustri, Technical University of Denmark, DK 2800 Lynghy, Denmark.

*Primary Examiner*—Arthur C. Prescott
*Attorney, Agent, or Firm*—Brooks Haidt Haffner & Delahunty

[57] ABSTRACT

Preparation of an aliphatic carboxylic acid having (n+1) carbon atoms, where n is an integer up to 6, may be achieved by contacting an aliphatic alcohol having n carbon atoms or a reactive derivative thereof with carbon monoxide, in the presence of a copper, nickel, iridium, rhodium or cobalt loaded mordenite zeolite catalyst, at elevated temperature and at a pressure in the range 15 to 200 bars.

6 Claims, No Drawings

PROCESS FOR PREPARING CARBOXYLIC ACIDS

The present invention relates to a process for preparing a carboxylic acid having (n+1) carbon atoms by reacting an alcohol having n carbon atoms or a reactive derivative thereof with carbon monoxide in the presence of a metal exchanged or supported zeolite catalyst.

The preparation of eg acetic acid from methanol and carbon monoxide is a well known example of a carbonylation process and is one which is carried out commercially. On a commercial scale this is operated as a homogeneous liquid-phase process in which the carbonylation reaction is catalysed by a soluble rhodium/iodide complex and an alkyl iodide such as methyl iodide. The main drawbacks of this process are the use of iodide which can lead to corrosion problems and the difficulties associated with separation of the products and catalyst components from a single phase. Both of these drawbacks could be overcome if a heterogeneous gas phase process using an iodide free solid catalyst could be developed.

GB 1185453 discloses certain multiphase catalysts comprising a catalytically active metal including inter alia copper, rhodium and iridium supported on a wide range of carrier materials including silicas, aluminas, carbons, zeolites, clays and polymers. These multiphase catalysts are taught as being useful in the heterogeneous gas phase carbonylation of methanol to acetic acid in the presence of a halide promoter. A similar process is disclosed GB 1277242 although neither patent exemplifies the use of a zeolite in such a process.

U.S. Pat. No. 4,612,387 discloses a process for making monocarboxylic acids and esters comprising contacting carbon monoxide with a monohydric alcohol having from 1 to 4 carbon atoms in the presence of a crystalline aluminosilicate zeolite having a silica to alumina ratio of at least about 6 and a constraint index within the range of 1 to 12 under a pressure of at least 1 atmosphere. The most preferred zeolites according to this definition are ZSM-5, ZSM-11, ZSM-12, ZSM-38 and ZSM-35 with ZSM-5 being particularly preferred. Mordenite type zeolites, which have a constraint index of 0.4, ie outside the claimed range, are referred to in Example VI run 30 where the hydrogen form was shown not to be catalytically effective. The preferred zeolites defined in the patent are preferably modified to incorporate a Group IB, IIB, IVB or VIII metal of which the most preferred is copper.

J Catalysis, 71, 233–43 (1981) discloses the use of photoelectron spectroscopy (ESCA) to determine the activity of a rhodium mordenite catalyst and other supported rhodium catalysts towards carbonylation of methanol to acetic acid. However, the effect of reaction temperature and pressure on catalytic activity was not examined.

DE 3606169 discloses a process for the preparation of acetic acid, methyl acetate and/or dimethyl ether by carbonylation of anhydrous methanol, methyl acetate and/or dimethyl ether in the presence of cobalt containing zeolites or zeolites mixed with cobalt salts. The carbonylation is optionally carried out in the presence of a halide. According to this patent preferred zeolites are those of the pentasil type whose pore sizes are intermediate between that of zeolite A on the one hand and zeolites X and Y on the other. The zeolites exemplified are again of the ZSM-5 type.

Finally Chemistry Letters pp 2047–2050 (1984) is concerned with the vapour phase carbonylation of methanol in the absence of a halogen promoter. Table 1 of this paper refers to three examples carried out at 200° C. and 10 bar pressure in which hydrogen mordenite and copper mordenite are used as catalysts. In all three cases yields were low relative to similar experiments employing a ZSM-5 based catalyst.

In view of the above-mentioned prior art, the problem to be solved is to develop a heterogeneous gas-phase process for preparing carboxylic acids from alcohols and carbon monoxide using a metal loaded zeolite catalyst, substantially in the absence of halogens or derivatives thereof, which is superior to the best processes using other zeolites previously described.

It has now been found that if the carbonylation process is carried out at temperatures in excess of 300° C. and pressures in excess of 15 bars then surprisingly catalysts derived from mordenite are superior to those based upon zeolite ZSM-5.

According to the present invention there is provided a process for preparing an aliphatic carboxylic acid having (n+1) carbon atoms, where n is an integer up to 6, which comprises contacting an aliphatic alcohol having n carbon atoms or a reactive derivative thereof with carbon monoxide substantially in the absence of the halogens or derivatives thereof in the presence of a catalyst consisting essentially of mordenite which has been ion-exchanged or loaded with copper, nickel, iridium, rhodium or cobalt characterised in that the process is carried out at a temperature in the range 300°–600° C. and at a pressure in the range 15 to 200 bars.

The present invention solves the problem defined above by using a modified mordenite catalyst at high temperatures and pressures to produce good yields of carboxylic acids and derivatives thereof. The finding that this can be achieved with mordenite by working at high temperature and pressure is surprising because from the work with ZSM-5 and zeolite Y described in the Chemistry Letters reference mentioned above, it would be expected that the effect of increasing the temperature would be merely to increase the yields of hydrocarbons at the expense of the carboxylic acid.

The process of the present invention involves the carbonylation of an aliphatic alcohol. Whilst any aliphatic alcohol can be used in principle the process is particularly applicable to aliphatic alcohols having up to 6, preferably up to 3, carbon atoms. Of this preferred group it is most preferred to use methanol since the corresponding carboxylic acid product, acetic acid, is a commercially important chemical. However the process claimed is equally applicable to the synthesis of propionic acid from ethanol and butanoic acid from normal propanol.

The aliphatic alcohol used can also be generated in situ on or near the catalyst by feeding a mixture of water and the ester of the aliphatic alcohol and the product carboxylic acid. Alternatively, a mixture of the corresponding ether and water can be used as feed.

The product of the process is either the corresponding aliphatic carboxylic acid having one extra carbon atom or eg the ester of this aliphatic carboxylic acid and the original aliphatic alcohol reactant. The aliphatic carboxylic can of course easily be liberated from the ester by known methods.

The purity of the carbon monoxide used is not deemed to be especially critical although it is desirable to use gas mixtures in which carbon monoxide is the main component. The presence of small amounts of nitrogen and the noble gases can be tolerated as can the amounts of hydrogen found in commercial samples of synthesis gas.

As mentioned above, the catalyst used in the process of the present invention is a mordenite zeolite which has been ion-exchanged, or otherwise loaded with copper, nickel, iridium, rhodium or cobalt. The structure of the zeolite mordenite is well known and defined for example in 'Atlas of Zeolite Structure Types' by W M Meier and D H Olson published by the Structure Commission of the International Zeolite Association in 1978. It is further characterised by having a constraint index of 0.4 and a silica to alumina ratio in the range 8:1 to 20:1. It is well known to those skilled in the art that the silica to alumina ratio may be increased by using de-alumination techniques, for example, by hydro-thermal treatment or acid leaching of the mordenite. Mordenite also possesses a characteristic X-ray powder diffraction pattern which will be well known to those skilled in the art. For the process of the present invention it is preferred that the mordenite has a silica to alumina ratio in the range 8:1 to 50:1, preferably in the range 10:1 to 30:1 and most preferably in the range 15:1 to 25:1.

Before use as a catalyst; the mordenite is ion-exchanged or otherwise loaded with copper, rhodium, iridium or cobalt. If the mordenite is to be ion-exchanged then up to 80% of the cation-exchangable sites on the zeolite may be exchanged with eg $Cu^{2+}$, $Ir^{3+}$ or $Rh^{3+}$ ions using well known techniques. It is preferred that the remaining cations in the exchanged mordenite are protons hence it is convenient to start the exchange process from the ammonium or hydrogen form.

As an alternative to ion-exchange, the ammonium or hydrogen form of the mordenite can be impregnated with a solution of the salt of the metal and thereafter dried. If the ammonium form is used, it is preferred to calcine the mordenite after loading or exchange. The amounts used are preferably such as to produce a catalyst having a metal content of 0.5 to 10% by weight based on the total catalyst.

In both of the cases mentioned above, it is preferably to activate the mordenite catalyst for at least one hour at elevated temperature under flowing nitrogen, carbon monoxide or hydrogen immediately before use.

The process of the present invention is suitably carried out by passing methanol vapour and carbon monoxide gas through a fixed or fluidized bed of the catalyst maintained at the required temperature and pressure. Such a process is carried out substantially in the absence of iodide in other words the iodide content of the feed gases and catalyst are less than 500 ppm preferably less than 100 ppm. The process is carried out at a temperature in the range 300 to 600° C. preferably 300 to 400° C. and at a pressure in the range 15 to 200 bars preferably 25 to 100 bars. The molar ratio of carbon monoxide to methanol in the feed to the catalyst is suitably in the range 1:1 to 60:1, preferably 1:1 to 30:1, most preferably 2:1 to 10:1. If fed to the catalyst bed in liquid form, the Liquid Hourly Space Velocity (LHSV) of the methanol feed should preferably be in the range 0.5 to 2.

In an embodiment of the present invention it has been found that the activity of he catalyst can be significantly increased by contacting the feed with a bed of alumina or silica-alumina immediately before the bed of catalyst. The volume ratio of this pre-bed to the catalyst bed is! suitably in the range 1:10 to 10:1 preferably 2:1 to 1:2.

The carboxylic acid produced by the process of the present invention can be removed in the form of a vapour and thereafter condensed to a liquid. Subsequently the carboxylic acid can be purified using standard distillation techniques.

The invention is now illustrated with reference to the following Examples.

The metal loaded zeolite catalysts were prepared by wet impregnation of metal salt solutions. The following examples show typical preparations of the acid form of mordenite and the copper, rhodium and iridium loaded acid forms of various zeolites.

EXAMPLE 1—Preparation of H-mordenite
($SiO_2/Al_2O_3 = 12.6$)

80 g of sodium form mordenite (ex Laporte grade M2, $SiO_2/Al_2O_3 = 12.6$) was slurried with 800 ml of 1.5 M $NH_4NO_3$ solution for 4 hours at 80° C. After this period the sample was filtered, washed with copious amounts of distilled water and dried at 100° C.. This procedure was repeated twice to produce the ammonium form. The ammonium form was then converted to the acid form by heating the material at 500° C. for 2 hours.

EXAMPLE 2—Preparation of Cu/H-mordenite (1)
($SiO_2/Al_2O_3 = 12.6$)

$Cu(NO_3)_2.3H_2O$ (6.88 g) was dissolved in 100 $cm^3$ of distilled water, this solution was slurried with 50.00 g of the ammonium form of the mordenite (prepared above). The mixture was evaporated to dryness, heated at 100° C. for 16 hours and then calcined at 500° C. for 2 hours. Chemical analysis revealed the solid to contain 3.8 wt% copper.

COMPARISON TEST A—Preparation of Cu/H-ZSM-5

The same procedure was followed as in example 2 except that the zeolite used was the ammonium form of ZSM-5 (ex PQ $SiO_2/Al_2O_3 = 35.0$).

COMPARISON TEST B—Preparation of Cu/H-Y

The same procedure was followed as in example 2 except that the zeolite used was the ammonium form of zeolite Y (ex Laporte, $SiO_2/Al_2O_3 = 3.1$).

EXAMPLE 3—Preparation of Rh/H-mordenite

243 $cm^3$ of a 0.01 M $RhCl_3$ solution was slurried with 25 g of ammonium form of the mordenite (prepared in Example 1). The mixture was evaporated to dryness and dried at 100° C. overnight. The solid was calcined in air at 500° C. for 2 hours. Chemical analysis showed that the solid contained 1.0% by weight rhodium.

EXAMPLE 4—Preparation of Ir/H-mordenite

130 $cm^3$ of a 0.01 M $IrCl_3$ solution was slurried with 25 g of the ammonium form of the mordenite (prepared in Example 1). The mixture was evaporated to dryness and dried at 100° C. overnight. The solid was then calcined at 500° C. for 2 hours.

EXAMPLE 5—Preparation of Cu/H-mordenite (2)
($SiO_2/Al_2O_3 = 20$)

The same procedure was followed as in example 2 except that the zeolite used was the ammonium form of the mordenite of composition $SiO_2/Al_2O_3 = 20$ (ex PQ).

EXAMPLE 6—Preparation of Cu/H-mordenite (3) (SiO2/A12O3=20)

The same procedure was followed as in example 2 except that the amount of copper nitrate used was increased to 13.78 g.

EXAMPLE 7—Catalytic Testing

To investigate the catalytic activity of these materials for the non-iodide carbonylation of methanol to acetic acid the zeolites were tested in a pressure flow reactor. The zeolite catalysts were pelleted to a size of 250–850 μm) and loaded into the reactor. A catalyst pre-bed was also employed to ensure efficient mixing/heating of the reactants, the pre-beds employed were anti-bumping granules (ex BDH) used in runs 1–7 and gamma-alumina (surface area=280 m2/g, particle size=250–850 μm used in runs 8–11. The gamma-alumina pre-bed was also used to convert the methanol to dimethylether prior to the catalyst bed. The catalysts were activated under flowing nitrogen (100 cm3/min) at 350° C. for 16hrs and then reduced under carbon monoxide (200 cm3/min) at 350° C. for 2 hours. The system was then pressurised up to 25 atm using a back pressure regulator. The flow rate of the carbon monoxide was adjusted to 400 cm3/min (GHSV=2200) and methanol was fed to the reactor via a pump (rate=0.15ml/min). The liquid/solid products and reactants were collected in a cooled trap, while gaseous products and reactants were sampled downstream of the back pressure regulator. The reaction was sampled every three hours. All the samples were analysed off-line using gas chromatography. The level of carbon dioxide, formed as a by-product of the competing Water Gas Shift Reaction, was relatively low being in the range 1 to 10 mol % of the total moles of product. Results of catalytic testing are shown in Tables 1–6.

TABLE 1

Methanol carbonylation over Cu/H-ZSM-5, Cu/H-Y, Cu/H-mordenite(1), Cu/Na-mordenite, H-moerdenite, Rh/H-mordenite and Ir/H-mordenite

| Run | Catalyst | MeOH Conv. | Product selectivity (C-mol %) | | | |
|---|---|---|---|---|---|---|
| | | | DME | C1–C17 Hydrocarbons[a] | MeOAc | AcOH |
| 1 | Cu/H-ZSM-5 | 99.3 | 0.0 | 99.7 | 0.0 | 0.3 |
| 2 | Cu/H-Y | 92.6 | 88.8 | 10.8 | 0.3 | 0.1 |
| 3 | Cu/H-mord | 99.1 | 21.0 | 71.2 | 4.1 | 3.7 |
| 4 | Cu/Na-mord | 94.0 | 93.2 | 6.6 | 0.2 | 0.0 |
| 5 | H-mord | 99.5 | 0.9 | 96.7 | 0.5 | 2.0 |
| 6 | Rh/H-mord | 98.6 | 13.1 | 83.1 | 2.5 | 1.3 |
| 7 | Ir/H-mord | 100.0 | 6.3 | 90.2 | 0.6 | 2.9 |

Conditions: Time = 3 h, 350° C. 25 bar, GHSV = approximately 2200, LHSV = 0.9, CO/MeOH = 4.4

$$C - mol\ \% = \frac{moles\ of\ product \times number\ of\ MeOH\ based\ carbons\ in\ molecule}{moles\ of\ MeOH\ converted}$$

[a]Also contains acetone and other oxygenates (less than 8 mol %)

TABLE 2

Catalyst Lifetime Study of Run 3

| Time/h | MeOH Conv. | Product selectivity (C-mol %) | | | |
|---|---|---|---|---|---|
| | | DME | C1–C17 Hydrocarbons[a] | MeOAc | AcOH |
| 3 | 99.1 | 21.0 | 71.2 | 4.1 | 3.7 |
| 6 | 93.6 | 90.9 | 2.7 | 5.4 | 1.0 |
| 9 | 92.2 | 95.9 | 0 | 3.7 | 0.4 |
| 12 | 88.6 | 97.2 | 0 | 2.4 | 0.4 |

Conditions: 350° C. 25 bar, GHSV = 2280, LHSV = 0.9, CO/MeOH = 4.4
[a]Also contains acetone and other oxygenates (less than 8 mol %)

TABLE 3

Run 8 using Cu/H-mordenite(1) and a gamma-alumina pre-bed

| Time/h | MeOH Conv. | Product selectivity (C-mol %) | | | |
|---|---|---|---|---|---|
| | | DME | C1–C17 Hydrocarbons[a] | MeOAc | AcOH |
| 3 | 99.5 | 16.3 | 72.1 | 3.3 | 8.3 |
| 6 | 85.3 | 74.3 | 6.5 | 15.3 | 3.9 |

Conditions: 350° C. 25 bar, GHSV = 2216, LHSV = 0.9, CO/MeOH = 4.4
[a]Also contains acetone and other oxygenates (less than 8 mol %)

TABLE 4

Run 9: Effect of CO/MeOH ratio on the carbonylation activity of Cu/H-mordenite(1) plus gamma-alumina pre-bed

| Time/h | MeOH Conv. | Product selectivity (C-mol %) | | | |
|---|---|---|---|---|---|
| | | DME | C1 to C17 Hydrocarbons[a] | MeOAc | AcOH |
| 3 | 96.9 | 53.5 | 25.9 | 13.7 | 7.1 |
| 6 | 89.0 | 87.2 | 1.2 | 8.8 | 2.8 |
| 9 | 85.2 | 91.0 | 1.1 | 6.2 | 1.7 |

Conditions: CO/MeOH = 8.8, 350° C., 25 bar, GHSV = 4376, LHSV = 0.9
[a]Also contains acetone and other oxygenates (less than 8 mol %)

TABLE 5

Run 10 using Cu/H-mordenite(2) and a gamma-alumina pre-bed to show the effect of the silica to alumina ratio on carbonylation activity

| Time/h | MeOH Conv. | Product selectivity (C-mol %) | | | |
|---|---|---|---|---|---|
| | | DME | C1 to C17 Hydrocarbons[a] | MeOAc | AcOH |
| 3 | 99.2 | 0.0 | 71.5 | 0.3 | 28.3 |
| 6 | 99.0 | 6.0 | 46.3 | 22.5 | 25.2 |
| 9 | 97.9 | 29.4 | 32.5 | 30.0 | 8.0 |

Conditions: Time = 3 h, 350° C., 25 bar, GHSV = 4410, LHSV = 0.9, CO/MeOH = 8.8
[a]Also contains acetone and other oxygenates (less than 8 mol %)

TABLE 6

Run 11 using Cu/H-mordenite(3) and a gamma-alumina pre-bed to show the effect of copper loading on carbonylation activity

| Time/h | MeOH Conv. | Product selectivity (C-mol %) | | | |
|---|---|---|---|---|---|
| | | DME | C1 to C17 Hydrocarbons[a] | MeOAc | AcOH |
| 3 | 100 | 0.0 | 85.4 | 0.4 | 14.2 |
| 5.4 | 97.9 | 7.6 | 40.3 | 19.0 | 33.1 |
| 8.4 | 93.9 | 23.2 | 26.2 | 27.9 | 22.7 |

Conditions: CO/MeOH = 9.1, 350° C., 25 bar, GHSV = 4545, LHSV = 0.9
[a]Also contains acetone and other oxygenates (less than 8 mol %)

I claim:

1. A process for preparing an aliphatic carboxylic acid having (n+1) carbon atoms and derivative thereof, where n is an integer up to 6, which comprises contacting an aliphatic alcohol having n carbon atoms or a reactive derivative thereof with carbon monoxide substantially in the absence of halogens or derivatives thereof in the presence of a catalyst consisting essentially of a mordenite zeolite which has been ion-exchanged or loaded with copper, nickel, iridium, rhodium or cobalt characterised in that the process is carried out at a temperature in the range 300 to 600° C. and at a pressure in the range 15 to 200 bars.

2. A process according to claim 1 in which the aliphatic alcohol is methanol or a reactive derivative thereof.

3. A process according to any one of claims 1 and 2 in which the mordenite zeolite has a silica to alumina ratio in the range 10:1 to 30:1.

4. A process according to any one of the preceding claims in which the catalyst has a metal content of 0.5 to 10% by weight based on the total weight of catalyst.

5. A process according to any one of the preceding claims in which carbon monoxide gas and methanol vapour are fed through a fixed or fluidized bed of the catalyst substantially in the absence of iodide.

6. A process according to any one of the preceding claims in which the aliphatic alcohol or reactive derivative thereof and carbon monoxide are contacted with a bed of alumina or silica-alumina immediately before a bed of the catalyst.

* * * * *

UNITED STATES PATENT AND TRADEMARK OFFICE
CERTIFICATE OF CORRECTION

PATENT NO. : 5,420,345
DATED : May 30, 1995
INVENTOR(S) : WARREN J. SMITH

It is certified that error appears in the above-indentified patent and that said Letters Patent is hereby corrected as shown below:

Col. 3, line 67, change "is!" to --is--

Col. 5, Table 1 heading, correct the spelling of "H-mordenite"

In each of Tables 1, 2 and 3, in the line giving "Conditions", insert a comma (,) after "350°C."
Col. 6
Claim 1, line 2, change "derivative" to --derivatives--

Signed and Sealed this

Nineteenth Day of December, 1995

Attest:

BRUCE LEHMAN

Attesting Officer

Commissioner of Patents and Trademarks